（12）United States Patent
Lumauig

(10) Patent No.: US 7,351,301 B2
(45) Date of Patent: Apr. 1, 2008

(54) CATHETER AND METHOD FOR MAKING THE SAME

(75) Inventor: Rommel C. Lumauig, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 392 days.

(21) Appl. No.: 11/093,668

(22) Filed: Mar. 29, 2005

(65) Prior Publication Data

US 2005/0167032 A1    Aug. 4, 2005

Related U.S. Application Data

(62) Division of application No. 09/747,817, filed on Dec. 22, 2000, now Pat. No. 6,893,456.

(51) Int. Cl.
*B29C 65/00* (2006.01)

(52) U.S. Cl. .............................. 156/272.2; 156/272.8; 156/293; 156/294; 606/194; 606/103

(58) Field of Classification Search ............. 156/272.2, 156/275.1, 272.8, 293, 294; 264/512, 248, 264/482; 606/194, 103; 623/1.11
See application file for complete search history.

(56) References Cited

U.S. PATENT DOCUMENTS

| | | | |
|---|---|---|---|
| 4,892,519 A | 1/1990 | Songer et al. | |
| 5,267,959 A * | 12/1993 | Forman | 604/103 |
| 5,279,526 A | 1/1994 | Gundlach | |
| 5,279,562 A | 1/1994 | Sirhan et al. | |
| 5,496,275 A | 3/1996 | Sirhan et al. | |
| 5,533,968 A | 7/1996 | Muni et al. | |
| 5,545,149 A * | 8/1996 | Brin et al. | 604/265 |
| 5,569,201 A | 10/1996 | Burns | |
| 5,605,543 A * | 2/1997 | Swanson | 604/102.02 |
| 5,728,065 A | 3/1998 | Follmer et al. | |
| 5,743,875 A * | 4/1998 | Sirhan et al. | 604/96.01 |
| 5,759,191 A | 6/1998 | Barbere | |
| 5,833,672 A | 11/1998 | Kawata et al. | |
| 5,922,003 A * | 7/1999 | Anctil et al. | 606/170 |
| 5,951,513 A | 9/1999 | Miraki | |
| 6,013,069 A | 1/2000 | Sirhan et al. | |
| 6,027,475 A | 2/2000 | Sirhan et al. | |
| 6,096,056 A | 8/2000 | Brown | |
| 6,179,856 B1 | 1/2001 | Barbere | |
| 6,585,687 B1 | 7/2003 | Shkolnik | |

FOREIGN PATENT DOCUMENTS

WO    WO 93/20882    10/1993

* cited by examiner

*Primary Examiner*—Jeff H. Aftergut
*Assistant Examiner*—Daniel McNally
(74) *Attorney, Agent, or Firm*—Fulwider Patton LLP

(57) ABSTRACT

The invention is generally directed to an intraluminal catheter with an improved transition between a proximal shaft portion and a more flexible distal shaft portion and a method for making the same. The improvement provides enhanced flexibility, reduced bunching, and kink-resistance, thus, facilitating advancement through tortuous anatomy. The present catheters may be used for either or both angioplasty and stent deployment.

7 Claims, 4 Drawing Sheets

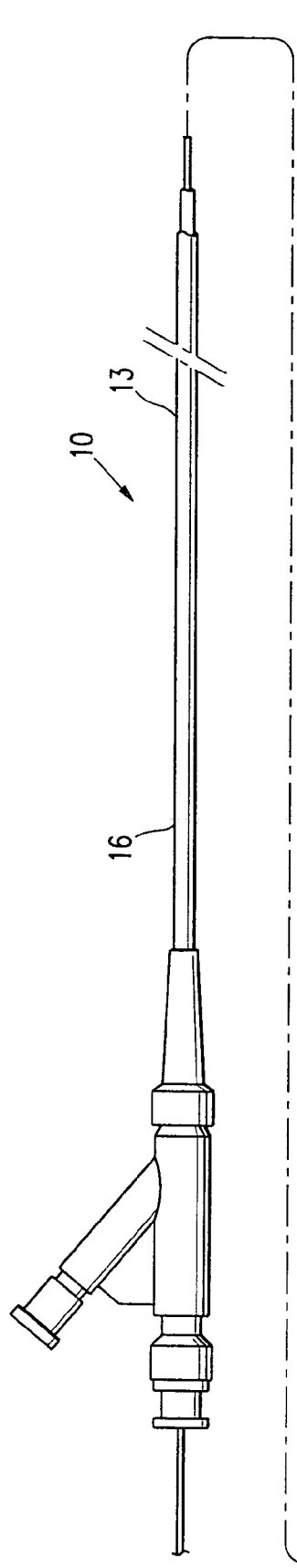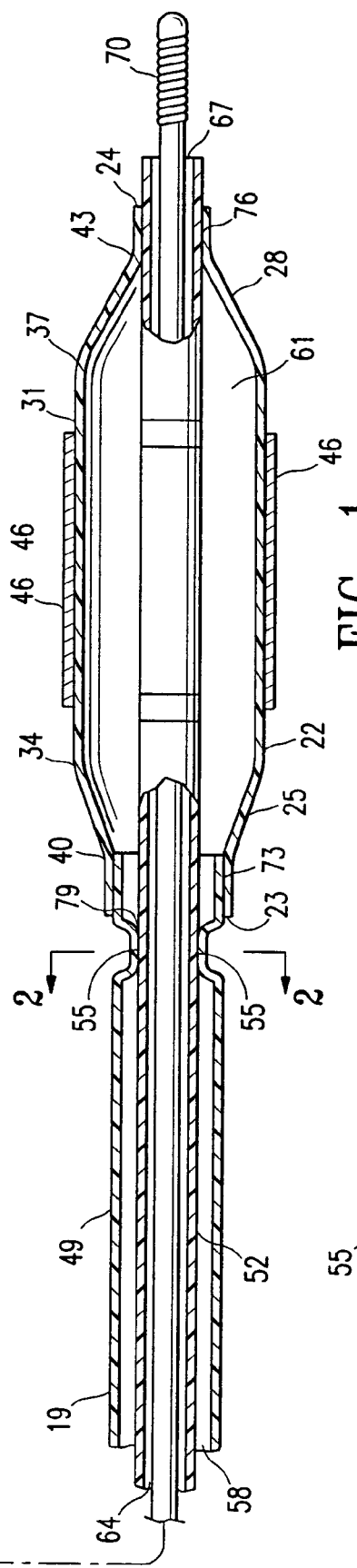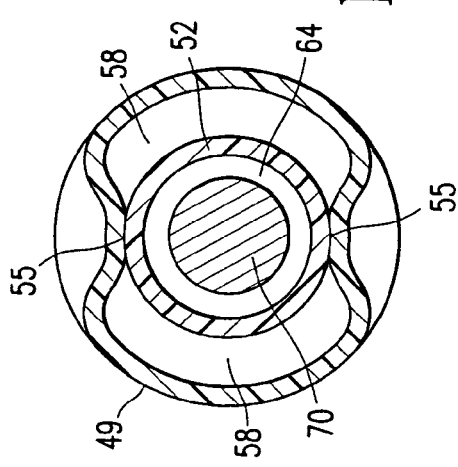

CATHETER AND METHOD FOR MAKING THE SAME

This application is a divisional of, and claims the benefit of the priority date of application Ser. No. 09/747,817, filed Dec. 22, 2000, now U.S. Pat. No. 6,893,456.

FIELD OF INVENTION

The invention relates to the field of intravascular catheters, and particularly to a catheter suitable for angioplasty and/or stent deployment, and the like.

BACKGROUND OF THE INVENTION

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to keep open a stenosed vessel, and strengthen the dilated area by remaining inside the vessel. Instead of first using one catheter to dilate the body lumen and a second catheter to deploy the stent after the dilatation, the stent may be mounted on a balloon catheter and deployed at the same time the balloon is inflated to dilate the stenotic region.

Conventional balloon catheters for intravascular procedures, such as angioplasty and stent delivery, frequently have relatively stiff proximal shaft sections to facilitate advancement of the catheter within the patient's body lumen and a relatively flexible distal shaft sections to facilitate passage through tortuous anatomy such as distal coronary and neurological arteries without damage to the luminal wall. The improved distal flexibility allows the device to turn tight corners along the vasculature without applying large forces against the wall of the vessels, thus minimizing the surface friction between the catheter and the vessel, thus allowing more distal access. This optimization of flexibility may aggravate other problems such as buckling (i.e., catheter tendency to fold easily at transition areas when push is transmitted through it) of the catheter and/or bunching of the balloon (tendency of the balloon to fold back upon itself when a columnar force is applied to it) at transition areas, such as areas having a discontinuity in their bending stiffness, thus leading to diminished capability of the catheter to navigate tight radius turns in the vasculature.

The above problems can be more pronounced when the catheter is designed for stent delivery, as balloon sections immediately proximal or distal to the stent can undergo bunching or buckling upon application of force as the catheter is being navigated through the anatomy.

Therefore, what has been needed is a catheter with improved push performance, in particular in the transition areas. The present invention satisfies these and other needs.

SUMMARY OF THE INVENTION

The invention is generally directed to an intraluminal catheter with an improved transition between a proximal shaft portion and a more flexible distal shaft portion and a method for making the same. The improvement provides enhanced flexibility and kink-resistance, thus, facilitating advancement through tortuous anatomy. The present catheters may be used for either or both angioplasty and stent deployment.

BRIEF DESCRIPTION OF THE DRAWINGS

FIG. 1 is a schematic, elevational view partially in section, of a catheter system embodying features of the invention.

FIG. 2 is a transverse cross sectional view of the catheter system of FIG. 1 taken along lines 2-2.

DETAILED DESCRIPTION OF THE INVENTION

Figure 4:
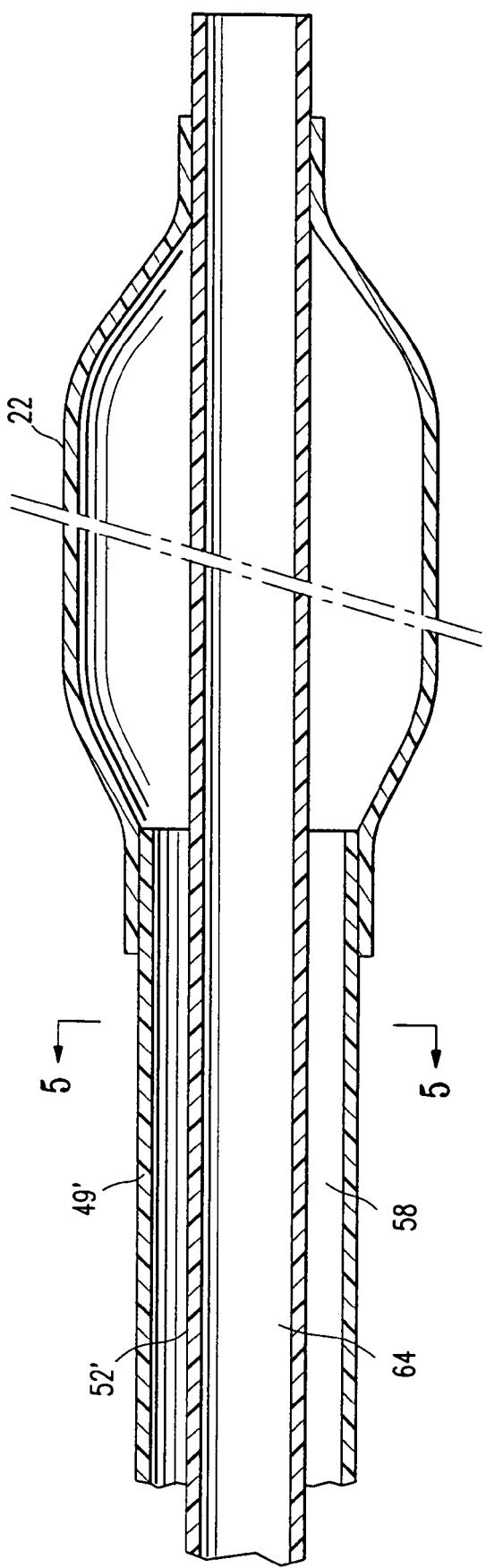
FIG. 4 is a transverse cross sectional view of a catheter system before undergoing the process of the present invention.

In the embodiment features of which are illustrated in FIGS. 1 and 2, the catheter 10 of the present invention is a balloon catheter including an elongated catheter shaft 13 having a proximal shaft section 16 and a distal shaft section 19 and an inflatable balloon 22 having proximal and distal ends 23 and 24 and being disposed on a distal portion of the distal shaft section 19 in surrounding relationship thereto. The balloon 22 has a proximal tapered region 25 and a distal tapered region 28 and an intermediate region 31 longitudinally disposed between the proximal and distal tapered regions 25 and 28. The proximal and distal tapered regions 25 and 28 each has a first end 34 and 37, respectively, and a second end 40 and 43 opposite their respective first ends, 34 and 37. The catheter 10, as shown further includes a stent 46 mounted on at least a portion of the intermediate region 31 to form a stent delivery catheter system.

In the embodiment shown, the catheter shaft 13 comprises an outer tubular member 49, and an inner tubular member 52 extending at least within a distal portion of the distal shaft section 19, the outer and inner tubular members 49 and 52 being partially attached at a juncture 55 proximally the balloon proximal end 23. Preferably, the outer and inner tubular members are attached at more than one juncture, the junctures being radially spaced apart. The junctures can extend along the same length or can be longitudinally set apart. Preferably, the junctures are disposed radially at substantially equal distance from one another.

The outer and the inner tubular members together define an inflation lumen 58, extending to a location spaced proximal to a distal end of the shaft 13, in fluid communication with an interior 61 of the balloon 22.

A guidewire lumen 64 extends within a least a distal portion of the inner tubular member 52 to an open distal end 67 of the catheter 10 for slidably receiving a guidewire 70 therein.

The balloon 22 is sealingly secured to the shaft 13 by one or more bonds, preferably, fusion bonds 73 and 76, at or near either or both the proximal and distal balloon second ends 40 and 43. The one or more bonds 73 and 76 are each formed at an interface between the shaft 13 and the balloon 22. The balloon 22 is bonded, preferably fusion bonded, to the outer tubular member 49 by the proximal fusion bond 73, and to the inner tubular member 52 by the distal fusion bond 76.

The juncture 55, preferably has a longitudinal dimension ranging from about 1 to about 4 millimeter (mm), preferably from about 2 to about 4, and most preferably from about 1 to about 2 mm; and a radial dimension ranging from about 0.5 to about 3 mm, preferably 1 to about 2 mm. A distal end 79 of the juncture 55 is proximally spaced apart from the balloon proximal end 23 in a range of about zero to about 3 mm, preferably from about zero to about 1 mm.

Figure 5:
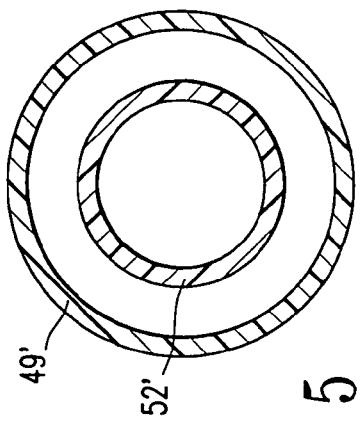
FIG. 5 is a transverse cross sectional view of the catheter system of FIG. 4 taken along lines 5-5.
Figure 3:
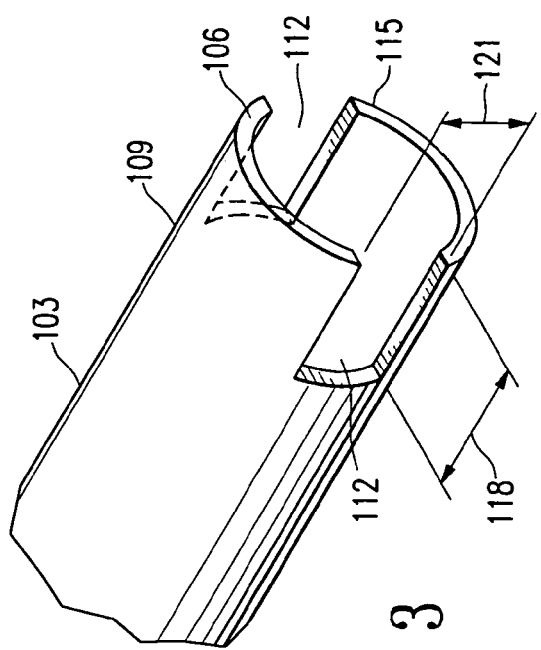
FIG. 3 is a schematic, elevational view partially in section, of a tool used in the process of the present invention.
Figure 6:
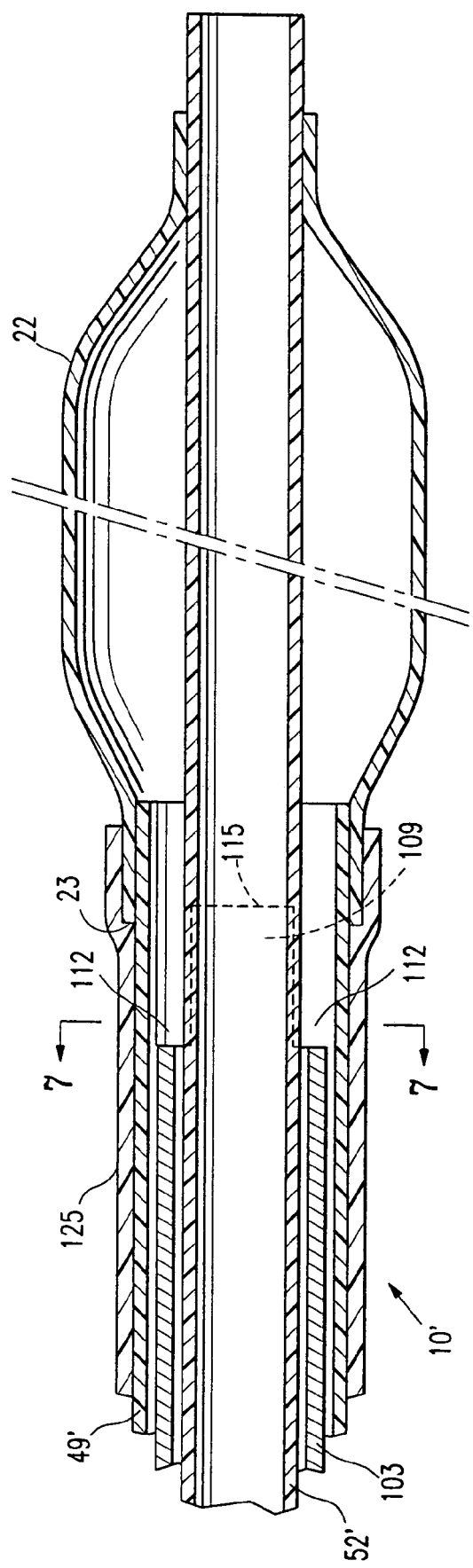
FIG. 6 is schematic, elevational view partially in section, of the catheter of FIG. 5 with the tool of FIG. 3 inserted therein showing a shrink tubing disposed on a portion of the exterior surface of the catheter.
Figure 7:
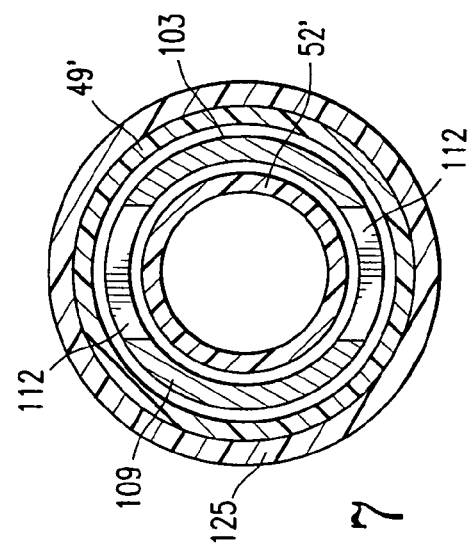
FIG. 7 is a transverse cross sectional view of the catheter system of FIG. 6 taken along lines 7-7 before the partial attachment of the inner and outer members.
Figure 8:
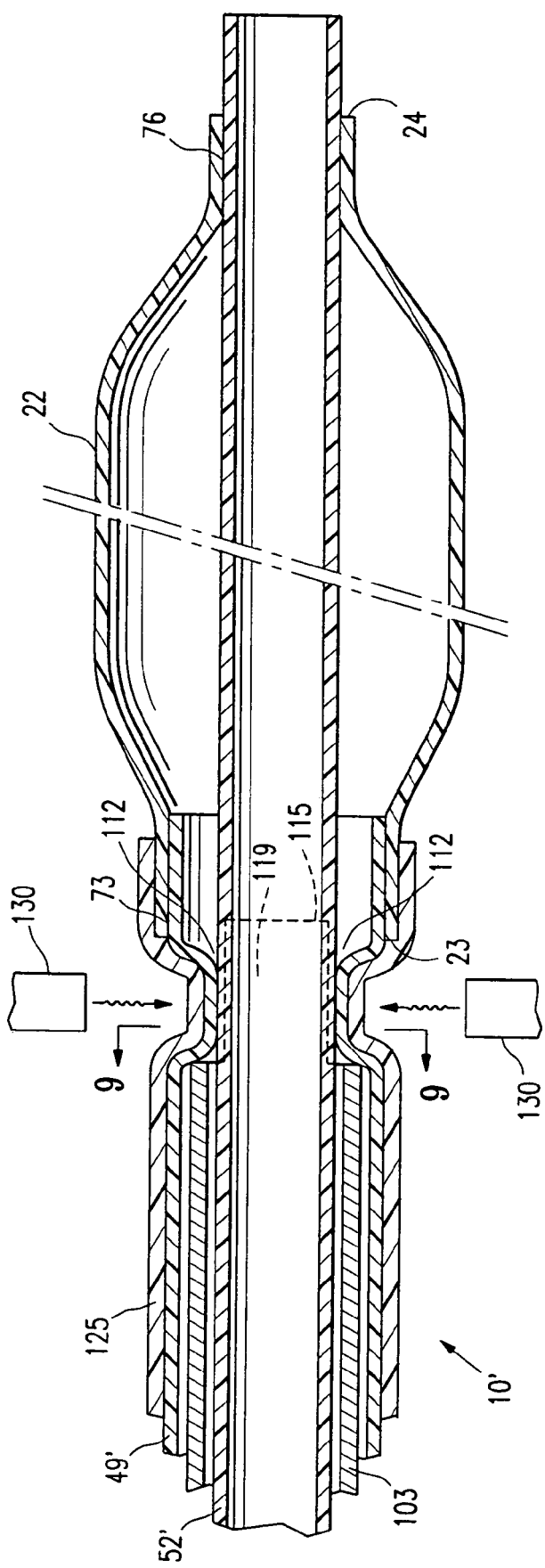
FIG. 8 is schematic, elevational view partially in section, of the catheter of FIG. 6 with the desired area being heated to induce shrinking and forming a tight fit between the surfaces.
Figure 10:
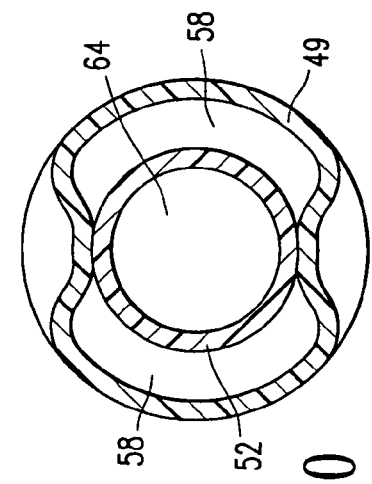
FIG. 10 illustrates the catheter transverse cross sectional view shown in FIG. 9 after the tool of FIG. 3 is removed.
Figure 9:
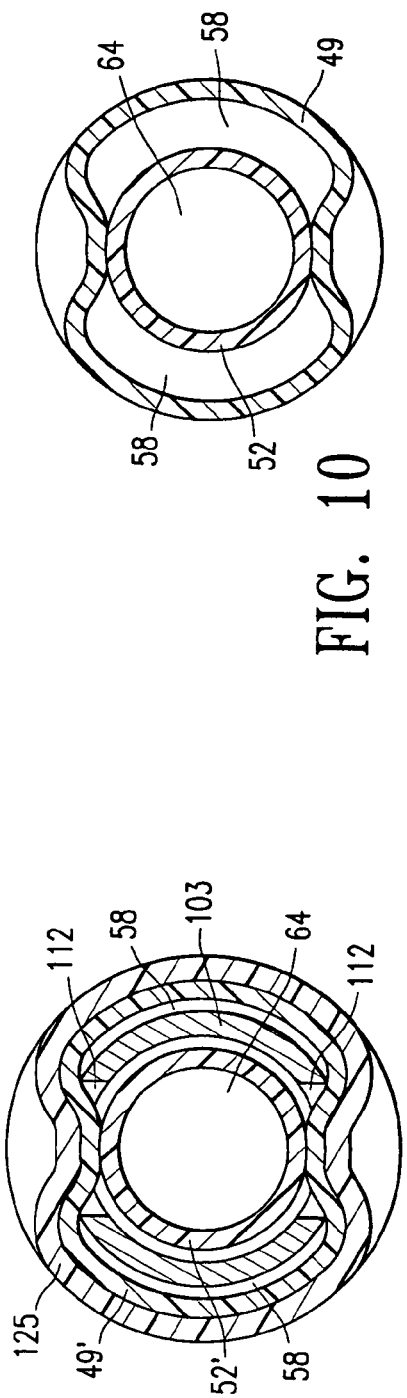
FIG. 9 is a transverse cross sectional view of the catheter system of FIG. 8 taken along lines 9-9 after the partial attachment of the inner and outer members with the tool of FIG. 3 still in place.

Now referring to FIGS. 3 through 10, in the method of forming the catheter 10 of the invention, a hollow mandrel 103 is provided having a longitudinal dimension sufficiently long to enable insertion and retraction of the same to and from a catheter 10'. By way of example, in one embodiment, the mandrel has a longitudinal dimension ranging from about 20 to 147 centimeters (cm), preferably a length ranging from about 110-140 cm in an over the wire type catheter, and a length ranging from about 30 to about 40 cm in a rapid exchange type catheter. The mandrel 103 has an outer diameter sufficiently smaller than an inner diameter of an outer tubular member 49', and an inner diameter sufficiently larger than an outer diameter of an inner tubular member 52' such that it can be slidably inserted in and out of the catheter 10'. By way of example, in one embodiment, the mandrel has an inner diameter and an outer diameter of 0.018 and 0.056 inches, respectively; preferably, 0.022 and 0.028 inches, respectively. The mandrel 103, preferably, has a thickness 106 ranging from about 0.5 to about 8 mm, preferably ranging from about 1 to about 3 mm.

The mandrel 103 at distal portion 109 has at least one cutaway strip 112, preferably, at least two cutaway strips extending from a distal end 115 to a location proximal to the distal end 115. In a preferred embodiment, the cutaway strips have a longitudinal dimension 118 ranging from about 1 to about 20 mm, preferably from about 5 to about 10 mm; and a radial dimension 121 ranging from about 1 to about 2 mm, preferably from about 1 to about 1.5 mm.

The mandrel 103 is slid over the inner tubular member 52' and is disposed between the outer and inner members 49' and 52' of the catheter 10' with the distal end 115 of the tubular member 103 extending distally beyond the balloon proximal end 23.

The distal end 115 of the mandrel 103 can be longitudinally spaced apart from the balloon proximal end 23 in a range from about 0.1 to about 2 mm, preferably from about 0.2 to about 1 mm.

A protective sleeve such as shrink tubing 125 is placed around at least a portion of the catheter 10' covering at least the area including the distal portion 109 of the mandrel 103. The desired area is heated to induce shrinking and to form a tight fit between the surfaces to be bonded (e.g., outer tubular member 49' and the inner tubular member 52'). Heat sufficient to melt the substrates is controllably directed from a heat source 130 to the catheter assembly 10' to be bonded. For example, substantially monochromatic energy at a wave length of maximum spectral absorption of the materials forming at least the inner surface of the outer tubular member and at least the outer surface of the inner tubular member is controllably directed onto a predetermined length of the distal portion of the catheter distal shaft section to concentrate the monochromatic energy to form a juncture between a portion of the outer tubular member and a portion of the inner tubular member. The presently preferred fusion heat source is a $CO_2$ laser. The laser power is about 50 mW to about 250 mW, the laser rotation speed about the members to be bonded is about 75 to about 300, and the laser absolute focus is about 0.30 to about 0.50. The materials are heated at temperatures between about 100° C. to about 200° C. for about 30 to about 150 seconds. The melted substrates are then allowed to cool down and fuse together into a fusion bond, with the shrink tubing 125 and the mandrel 103 removed thereafter, resulting in catheter 10.

The outer tubular member, the inner tubular member, and the balloon are selected from any suitable material compatible with the materials to which they may be bonded.

By way of example, the balloon 22, may be formed of any suitably material including nylon or nylon blends; or polyamide/polyether block copolymers such as those available under the trade name Pebax from Atochem; polyesters; polyurethanes; and polycarbonate-urethanes (a thermoplastic elastomer formed as the reaction product of a hydroxyl terminated polycarbonate, an aromatic diisocyanate, and a low molecular weight glycol used as a chain extender) such as those available under the trade name Bionate from The Polymer Technology Group.

The outer tubular member 49 may be formed of a polymeric material, including nylons; polyether block amides such as those available under the trade name Pebax from Atochem; polyurethanes; polyester block copolymers (containing one or more of the following glycols) comprising hard segments of polyethylene-terephthalate or polybutylene-terephthalate, and soft segments of polyether such as polyethylene glycol, polypropylene glycol or polytetramethylene glycol ethers, such as those available under the tradename Hytrel from DuPont; polyesters available from Dutch State Mines under the trade name Arnitel; or blends thereof. The outer tubular member 49 is preferably formed at least in part of Nylon.

The inner tubular member 52 may be formed from any suitable material such as polyether block amides such as those available under the trade name Pebax, nylons, single or co-extrusions including high density polyethylene/low density polyethylene, and preferably, is of a tri-layer tubular construction including high density polyethylene as an inner layer; polyolefinic material, preferably, polyethylene based adhesive polymers such as ethylene-acrylic acid copolymers which sold commercially as PRIMACOR by Dow Chemical Co. or as ESCOR by EXXON or as PLEXAR by Quantum Chemical Corp., as the middle layer; and an outer layer formed of Pebax. In one embodiment, the inner tubular member, the outer tubular member, and the balloon are formed of the tri-layered structure (described above), nylon, and nylon; respectively.

All or most of the layers of the multilayered tubular member are preferably selected or modified so that they can be melt processed, e.g. coextruded, simultaneously or sequentially, and as a result the polymeric materials of the various layers should be compatible in this regard or made compatible by appropriate additives to the polymers.

The mandrel 103 is selected of a material that is not permanently bondable to the material of the outer and inner tubular members. The mandrel 103 is preferably formed of a metallic material such as stainless steel, preferably, formed of 304v stainless steel, coated stainless steel as for example Teflon coated or pyrelene coated stainless steel, NiTi alloy, MP35N, Elgiloy and the like; or a non-metallic material such as braided polyimide, and high strength polymers such as polyetheretherketone (PEEK), polyetherketone, and polyketone.

It will be apparent from the foregoing that, while particular forms of the invention have been illustrated and described, various modifications can be made without departing from the spirit and scope of the invention. Moreover, those skilled in the art will recognize that features shown in one embodiment may be utilized in other embodiments.

What is claimed is:

1. A method for forming a balloon catheter, comprising:
    providing a balloon catheter having an elongated shaft with proximal and distal shaft sections and an inflation lumen extending therein, an inflatable balloon on the distal shaft section and in surrounding relation thereto having proximal and distal ends, an intermediate section longitudinally disposed between the balloon proximal and distal ends, and an interior chamber in fluid communication with the inflation lumen, and an outer tubular member and an inner tubular member disposed within at least a portion of the outer tubular member, the outer and inner tubular members defining at least a portion of the inflation lumen, the inner tubular member having an inner lumen for slidably receiving a guidewire therein;
    disposing a hollow mandrel over the inner tubular member within the outer tubular member, the distal end of the hollow mandrel being distal to the balloon proximal end, and the mandrel having a proximal end, a distal end, a lumen, and at least one cutaway strip extending from the hollow mandrel distal end to a location proximal to the hollow mandrel distal end, such that the inner tubular member is within the lumen of the hollow mandrel and is exposed along the cutaway strip;
    providing a protective sleeve encircling the outer tubular member at a distal portion of the distal shaft section housing at least a portion of the mandrel including the cutaway strip, and forcing the inner surface of the outer tubular member radially inwardly against the outer surface of the inner tubular member at the cutaway strip;
    controllably directing heat from a heat source onto a predetermined length of the distal portion of the catheter distal shaft section to concentrate the heat at a portion of the outer tubular member and a portion of the inner tubular member to thereby melt the materials of at least the outer surface of the inner tubular member and the inner surface of the outer tubular member along the predetermined length;
    allowing the previously melted materials to cool and solidify to form a bond between the outer tubular member and the inner tubular member;
    removing the protective sleeve and the mandrel.

2. The method of claim 1 wherein the mandrel is formed of a material which is permanently not bondable to at least the inner surface of the outer tubular member and the outer surface of the inner tubular member.

3. The method of claim 2 wherein the mandrel is formed of a material selected from the group including stainless steel, 304v stainless steel, coated stainless steel, Teflon coated stainless steel, pyrelene coated stainless steel, NiTi alloy, MP35N, Elgiloy, braided polyimide, polyetheretherketone, polyetherketone, and polyketone.

4. The method of claim 1 wherein the mandrel is dimensioned to have an outer diameter sufficiently smaller than an inner diameter of the outer tubular member and an inner diameter sufficiently larger than an outer diameter of the inner tubular member to be slidably received within the outer tubular member over the inner tubular member.

5. The method of claim 1 wherein the mandrel has at least two cutaway portions.

6. The method of claim 1 wherein the heat source is a laser, and wherein heating the predetermined length comprises providing substantially monochromatic energy at a wave length of maximum spectral absorption of the materials forming at least the inner surface of the outer tubular member and at least the outer surface of the inner tubular member.

7. The method of claim 1 wherein the protective sleeve is heat shrink tubing and forcing the outer tubular member radially inwardly against the inner tubular member at the cutaway strip comprises heat shrinking the protective sleeve on the outer tubular member.

* * * * *